(12) United States Patent
Kono et al.

(10) Patent No.: US 11,337,910 B2
(45) Date of Patent: May 24, 2022

(54) PARTICULATE COMPOSITION COMPRISING CRYSTALLINE ALPHA, ALPHA-TREHALOSE DIHYDRATE, ITS PREPARATION AND USES

(71) Applicant: Hayashibara Co., Ltd., Okayama (JP)

(72) Inventors: Masaki Kono, Okayama (JP); Masahiro Fujimoto, Okayama (JP); Yutaka Akagi, Okayama (JP); Akiko Miyake, Okayama (JP); Toshio Ariyasu, Okayama (JP)

(73) Assignee: HAYASHIBARA CO., LTD., Okayama (JP)

( * ) Notice: Subject to any disclaimer, the term of this patent is extended or adjusted under 35 U.S.C. 154(b) by 979 days.

(21) Appl. No.: 16/071,137

(22) PCT Filed: Jan. 19, 2017

(86) PCT No.: PCT/JP2017/001718
§ 371 (c)(1),
(2) Date: Jul. 19, 2018

(87) PCT Pub. No.: WO2017/126598
PCT Pub. Date: Jul. 27, 2017

(65) Prior Publication Data
US 2021/0161791 A1   Jun. 3, 2021

(30) Foreign Application Priority Data
Jan. 20, 2016   (JP) .............................. JP2016-009278

(51) Int. Cl.
*A61K 8/60* (2006.01)
*A23L 29/10* (2016.01)
(Continued)

(52) U.S. Cl.
CPC ................. *A61K 8/60* (2013.01); *A23L 3/46* (2013.01); *A23L 29/10* (2016.08); *A61K 8/0241* (2013.01);
(Continued)

(58) Field of Classification Search
None
See application file for complete search history.

(56) References Cited

U.S. PATENT DOCUMENTS 5,916,371 A * 6/1999 Chaen ...................... A23G 4/10
127/29
5,919,668 A   7/1999 Mandai et al.

FOREIGN PATENT DOCUMENTS

EP   0636693 A2   7/1994
EP   2759600 A1   9/2012
(Continued)

OTHER PUBLICATIONS

"Treha™ trehalose Identity Preserved Food Grade", Jan. 9, 2011, Retrieved from the Internet: URL: http://msds.plantprod.com/document1960 [retrieved on Jun. 18, 2019].

*Primary Examiner* — Dominic Lazaro
(74) *Attorney, Agent, or Firm* — Browdy and Neimark, PLLC

(57) ABSTRACT

An object of the present invention is to provide a particulate composition containing crystalline α,α-trehalose dihydrate, having an advantageous emulsifying ability.
The above object is solved by providing a particulate composition comprising crystalline α,α-trehalose dihydrate, which consists of particles containing α,α-trehalose and maltose and/or maltotriose, wherein said particulate composition contains α,α-trehalose in an amount of 70% by weight or higher but 90% by weight or lower, on a dry solid basis; and maltose and/or maltotriose in a total amount of 3% by weight or higher, on a dry solid basis; and has a
(Continued)

degree of crystallinity for crystalline α,α-trehalose dihydrate of 25% or higher but less than 90%, when calculated based on its powder X-ray diffraction profile.

8 Claims, 3 Drawing Sheets

(51) Int. Cl.
  *A23L 3/46* (2006.01)
  *A61K 8/02* (2006.01)
  *A61Q 19/10* (2006.01)
  *C12P 19/12* (2006.01)
  *C12P 19/18* (2006.01)

(52) U.S. Cl.
  CPC .............. *A61Q 19/10* (2013.01); *C12P 19/12* (2013.01); *C12P 19/18* (2013.01); *A23V 2002/00* (2013.01)

(56) References Cited

FOREIGN PATENT DOCUMENTS

| | | |
|---|---|---|
| GB | 2339197 A | 7/1999 |
| JP | 10-168093 A | 6/1998 |
| JP | 3793590 B2 | 7/2006 |
| JP | 2014054209 A | 3/2014 |
| WO | 2013/062093 A1 | 5/2013 |

\* cited by examiner

PARTICULATE COMPOSITION COMPRISING CRYSTALLINE ALPHA, ALPHA-TREHALOSE DIHYDRATE, ITS PREPARATION AND USES

TECHNICAL FIELD

The present invention relates to a particulate composition containing crystalline α,α-trehalose dihydrate, its preparation and uses, particularly, to a particulate composition containing crystalline α,α-trehalose dihydrate, having an advantageous emulsifying ability, its preparation and uses.

BACKGROUND ART

Alpha, alpha-trehalose (α,α-trehalose, simply abbreviated as "trehalose" throughout the specification, hereinafter) is a non-reducing disaccharide that two glucose molecules are bound via α,α-1,1 linkage. Since trehalose exhibits advantageous actions such as the inhibition of starch retrogradation, inhibition of the syneresis of foods, inhibition of the denaturation and clotting of proteins, stabilization of bubbles in Meringue and the like, inhibition of the denaturation of fats and oils, inhibition of the formation of heated odors from fruits and milk, protection of tissues from freezing, inhibition of the browning of fruits and vegetables, correction of tastes and flavors, it has been widely used for foods and beverages, cosmetics and quasi-drugs. Also, trehalose has been widely used for pharmaceuticals as an excipient for tablets, and a stabilizer for physiologically active substances.

Various methods have been conventionally known as processes for producing trehalose. For example, Patent Literature 1 discloses a process for producing a particulate composition containing crystalline trehalose dihydrate by allowing an α-glycosyltrehalose-forming enzyme and a trehalose-releasing enzyme to act on liquefied starch together with a starch-debranching enzyme and cyclomaltodextrin glucanotransferase, successively allowing glucoamylase to act on the resulting mixture to obtain a trehalose-containing saccharide solution, and crystallizing trehalose from the resulting trehalose-containing saccharide solution. Thus, the applicant of the present invention has now been producing a high-purity particulate composition containing crystalline trehalose dihydrate with a purity of 98.0% by weight or higher (a product name: "TREHA", commercialized by Hayashibara Co., Ltd., Okayama, Japan, called "a conventional particulate composition containing crystalline trehalose dihydrate", hereinafter), by using the process disclosed in Patent Literature 1, and commercializing as a material for food products, cosmetics, etc. The conventional particulate composition containing crystalline trehalose dihydrate has an extremely advantageous storage stability, hardly absorbs moisture even in the case of storing under a relatively high humidity condition, and is easy to use. However, the conventional particulate composition containing crystalline trehalose dihydrate did not substantially show an emulsifying ability, i.e., an ability of dispersing oily substance such as fats and oils in water.

PRIOR ART LITERATURE

Patent Literature

[Patent Literature 1] Japanese Patent No. 3793590

DISCLOSURE OF INVENTION

Object of the Invention

The present invention was made to solve the inconvenience in the above-identified conventional particulate compositions containing crystalline trehalose dihydrate, and to provide a particulate compositions containing crystalline trehalose dihydrate, having an advantageous emulsifying ability, its preparation and uses.

Means to Attain the Object

To solve the above objects, the present inventors continued studying by repeated trial and error about the emulsifying ability of a particulate composition containing crystalline trehalose dihydrate. In the course of the studying, the present inventors unexpectedly found that a particulate composition containing crystalline trehalose dihydrate, having an advantageous emulsifying ability, can be obtained by the steps of preparing a saccharide solution containing trehalose and maltose and/or maltotriose in a prescribed ratio, pulverizing the resulting saccharide solution by a spray-drying method, and converting a part of trehalose in an amorphous form into crystalline trehalose dihydrate by aging the resulting pulverized saccharide powder. Thus, they accomplished the present invention.

The present invention solves the above objects by providing a particulate composition containing crystalline trehalose dihydrate, which consists of particles containing trehalose and maltose and/or maltotriose, and has the following characteristics (1) to (3):

(1) containing trehalose in an amount of 70% by weight or higher but 90% by weight or lower, on a dry solid basis;

(2) containing maltose and/or maltotriose in a total amount of 3% by weight or higher, on a dry solid basis; and (3) having a degree of crystallinity for crystalline trehalose dihydrate of 25% or higher but less than 90%, when calculated based on its powder X-ray diffraction profile.

Judging from the process of spray-drying a saccharide solution containing prescribed amounts of trehalose and maltose and/or maltotriose, the particulate composition containing crystalline trehalose dihydrate of the present invention consists of particles containing trehalose and maltose and/or maltotriose.

The present invention solves the above objects by providing a process for producing a particulate composition containing crystalline trehalose dihydrate, having the above characteristics (1) to (3), which comprising the steps of preparing a saccharide solution containing trehalose in an amount of 70% by weight or higher but 90% by weight or lower, on a dry solid basis (hereinafter, abbreviated as "d.s.b.", in this specification), and maltose and/or maltotriose in a total amount of 3% by weight or higher, d.s.b.; pulverizing the resulting saccharide solution by a spray-drying method; crystallizing trehalose to form crystalline trehalose dihydrate by aging the resulting pulverized saccharide powder under relative humidity of 60% or higher for 7 days or longer; and drying the resulting particulate composition containing crystalline trehalose dihydrate.

Furthermore, the present invention solves the above objects by providing an emulsifying agent containing a particulate composition containing crystalline trehalose dihydrate, which consists of particles containing trehalose and maltose and/or maltotriose and has the above characteristics (1) to (3).

Effect of the Invention

Since the particulate composition containing crystalline trehalose dihydrate of the present invention has an advantageous emulsifying ability in comparison with a conventional particulate composition, it can be used widely in various fields such as foods and beverages, cosmetics, etc.

MODE FOR CARRYING OUT THE INVENTION

1. Definition of Terms

Figure 1:
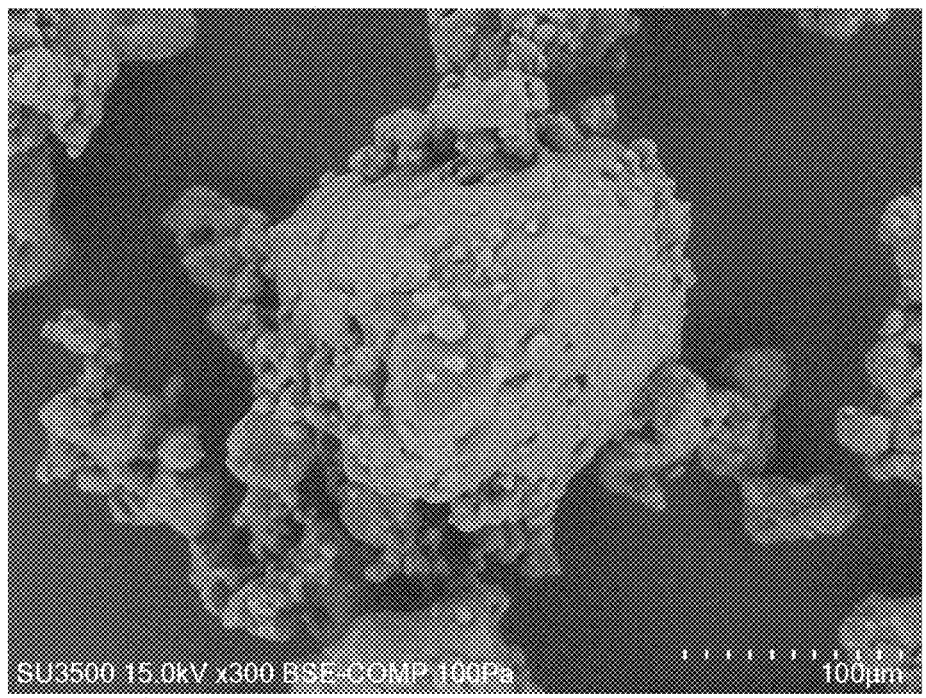
FIG. 1 is a photograph (300-fold magnification) of scanning electron microscope of Sample 1, a particulate composition containing crystalline trehalose dihydrate, obtained in Example 1-1 (which was aged under a relative humidity of 75% for 7 days).

Throughout the specification, the following terms mean as follows:

<Content (of Saccharide)>

The term "content (of saccharide)" as referred to as in the specification means a percentage (%) by weight of each saccharide to the total saccharides measured by the following analytical method for a saccharide composition: A sample saccharide is dissolved in purified water to give a solid concentration of one % by weight, and the resulting solution is filtrated by using a membrane filter with a pore size of 0.45 μm. Then, the resulting filtrate is subjected to the following saccharide composition analysis. The content of each saccharide is defined as the ratio of the peak area of each saccharide to the total peak area detected on HPLC chromatogram. The conditions of HPLC analysis are as follows:

Column: "MCL GEL CK04SS", commercialized by Mitsubishi Chemical Corp., Tokyo, Japan; (two column were connected in series)

Eluent: Purified water;
Column temperature: 80° C.;
Flow rate: 0.4 ml/min;
Detection: Differential refractometer: "RID-10A", commercialized by Shimadzu Corp., Kyoto, Japan;

The respective percentages (%) of peak area of trehalose, maltose, and maltotriose to the total peak area on the HPLC chromatogram is expressed as "trehalose content", "maltose content", and "maltotriose content".

<Degree of Crystallinity>

The term "a degree of crystallinity for crystalline trehalose dihydrate" as referred to as in the specification means a value defined by the following Formula [1].

Formula [1]:

$$\text{Degree of crystallinity (\%)} = \frac{H_s - H_0}{H_{100} - H_0} \times 100 \quad \text{[Equation 1]}$$

$H_{100}$: An analytical value for a degree of crystallinity, determined based on the powder X-ray diffraction profile for a powdered standard sample containing crystalline trehalose dihydrate, where the powdered standard sample consists substantially of crystalline trehalose dihydrate.

$H_0$: An analytical value for a degree of crystallinity, determined based on the powder X-ray diffraction profile for a powdered standard sample containing trehalose, where the powdered standard sample consists substantially of an amorphous form of trehalose.

$H_S$: An analytical value for a degree of crystallinity, determined based on the powder X-ray diffraction profile for, as a test sample, a powder containing trehalose.

In Formula [1], the powder X-ray diffraction profiles for the basis of determining analytical values $H_{100}$, $H_0$, and $H_S$ can be usually determined by a powder X-ray diffractometer equipped with a reflective or transmissive optical system. The powder X-ray diffraction profiles contain data for diffraction angles and diffraction strengths of crystalline trehalose dihydrate contained in a test or standard sample. The Hermans' method can be used as a method for determining the analytical data for the degrees of crystallinity from the powder X-ray diffraction profiles.

As "a powdered standard sample containing crystalline trehalose dihydrate, where the powdered standard sample consists substantially of crystalline trehalose dihydrate", for determining the analytical value $H_{100}$, there must be used a crystalline trehalose dihydrate in the form of a powder or a single crystal, which has a trehalose purity of 99.9% by weight or higher, exhibits characteristic diffraction peaks inherent to crystalline trehalose dihydrate on its powder X-ray diffraction pattern, and consists substantially of crystalline trehalose dihydrate. Examples of those in the form of a particulate composition or a single crystal include "TREHALOSE 999" (Code No: TH224, a trehalose purity of at least 99.9%), a product name of a particulate composition containing crystalline trehalose dihydrate, commercialized by Hayashibara Co., Ltd., Okayama, Japan, sold by the present applicant as an analytical reagent; and those in the form of a particulate composition containing crystalline trehalose dihydrate or in the form of a single crystal, obtained by recrystallizing the above product. For reference, when analyzed with a computer software for the Hermans' method, the powder X-ray diffraction profile of a particulate composition containing crystalline trehalose dihydrate, as the above-identified powdered standard sample, which consists substantially of crystalline trehalose dihydrate, gives an analytical value $H_{100}$, usually, ranging from about 50.6% to about 50.9%.

As "a powdered standard sample containing trehalose, where the powdered standard sample consists substantially of an amorphous form of trehalose" for determining the analytical value $H_0$, the one, which has a trehalose purity of 99.9% or higher and consists substantially of amorphous trehalose, is used. Examples of such a powdered standard sample include those which are obtained by dissolving the above-identified powdered standard sample for determining the aforesaid analytical value $H_{100}$ in an appropriate amount of refined water, concentrating the solution, freeze-drying the concentrate, and drying the resultant in vacuo up to give a moisture content of 2.0% or lower, when determined on the Karl Fischer method. With these treatments, it is known by experience that a particulate composition consisting substantially of an amorphous form of trehalose is obtained. In general, even a particulate composition consisting substantially of an amorphous form of trehalose, the analytical value should not necessarily be 0% because, when the particulate composition is subjected to a powder X-ray diffractometer and the resulting powder X-ray diffraction profile is analyzed on the Hermans' method, Vonk's method, etc., a part of the scattering light, derived from the amorphous form inherent to the algorithm of a computer software for operating the analytical methods, is calculated. For reference, when analyzed with a computer software for the Hermans' method, the powder X-ray diffraction profile of the particulate composition containing trehalose, as the above-identified powdered standard sample, which consists substantially of an amorphous form of trehalose, gives an analytical value $H_0$, usually, ranging from about 8.5% to about 8.7%.

The Hermans' method is described in detail in P. H. Hermans and A. Weidinger, *Journal of Applied Physics*, Vol. 19, pp. 491-506 (1948), and P. H. Hermans and A. Weidinger, *Journal of Polymer Science*, Vol. 4, pp. 135-144 (1949).

<Specific Surface Area>

The term "specific surface area" as referred to as in the specification means a surface area per unit mass of a particulate composition. About two grams of a particulate composition is dried in vacuo at 40° C. for 15 hours by using "BELPREP-vac II", a pretreatment device for the gas adsorption isotherm, commercialized by MicrotracBEL Corp., Osaka, Japan, and then the dried particulate composition is subjected to a conventional gas adsorption isotherms using nitrogen, using "BELSORP-mini II" an automatic specific surface area/pore size distribution analyzer, commercialized by MicrotracBEL Corp., Osaka, Japan. Specific surface area is defined as the surface area per one gram of the particulate composition, obtained by analyzing the above measurement value by the conventional BET method.

<Particle Size Distribution>

The term "particle size distribution" as referred to as in the specification means percentages (% by weight) of powder for each particle size, determined by the following method: Sieves with opening sizes of 425, 300, 212, 150, 106, 75 and 53 μm, which are compliant with Japanese Industrial Standards (JIS Z 8801-1), are accurately weighed, stacked in the above-identified order, and mounted on a ro-tap sieving shaker. A prescribed amount of weighed sample is placed on the uppermost sieve (having an opening size of 425 μm) in the stacked sieves, followed by shaking the sieves for 15 min while keeping the stacked state. Thereafter, each of the stacked sieves was accurately weighed again, and the weight of the sample collected on each of the sieves was determined by subtracting the weight of each of the sieves before loading on it the sample from the weight of the corresponding each of the sieves after shaking. Particle size distribution is expressed by calculating the weight percentage (%) of each of the weights of the particulate compositions with respective particle sizes collected on each of the sieves to the weight of the sample loaded on the uppermost sieve. For example, metal sieves, produced by Kabushiki Gaisha Iida Seisaku-sho, Tokyo, Japan, can be used as a sieves, and "R-1", a product name of a ro-tap sieving shaker, produced by Kabushiki Gaisha Tanaka Kagaku Kikai Seizo-sho, Osaka, Japan, can be used as a ro-tap sieving shaker.

<Emulsifying Ability>

The term "emulsifying ability" as referred to as in the specification means an ability of dispersing oil into water. The value of the emulsifying ability is defined as the turbidity (Absorbance at 720 nm) of emulsion obtained by the steps of mixing 5 parts by weight of the particulate composition and one part by weight of corn oil, successively admixing with 500 parts by weight of purified water, and stirring the mixture. The higher turbidity (Absorbance at 720 nm) of emulsion means a higher emulsifying ability. Concretely, the emulsifying ability can be measured, for example, by the steps of mixing 0.25 g of the particulate composition and 0.05 g of corn oil (a reagent grade, commercialized by FUJIFILM Wako Pure Chemical Corporation, Osaka, Japan), successively admixing with 25 g of purified water, stirring the mixture, and measuring the turbidity (Absorbance at 720 nm) of the resulting emulsion by using "UV-1800", a spectrophotometer commercialized by Shimadzu Corporation, Kyoto, Japan.

<Aging>

The term "aging" as referred to as in the specification means a process for converting an amorphous saccharide into crystalline saccharide by keeping an amorphous saccharide or a powder containing the same under prescribed temperature and humidity conditions and prescribed time period, and for proceeding the crystallization of the saccharide.

2. Particulate Composition Containing Crystalline Trehalose Dihydrate

The particulate composition containing crystalline trehalose dihydrate with advantageous emulsifying ability and storage stability, found by the inventors, consists of particles containing trehalose and maltose and/or maltotriose, and has the following characteristics (1) to (3):

(1) containing trehalose in an amount of 70% or higher but 90% by weight or lower, on a dry solid basis;
(2) containing maltose and/or maltotriose in a total amount of 3% by weight or higher, d.s.b.; and
(3) having a degree of crystallinity for crystalline trehalose dihydrate of 25% or higher but less than 90%, when calculated based on its powder X-ray diffraction profile.

The first characteristic of the particulate composition containing crystalline trehalose dihydrate of the present invention is that the particulate composition consists of particles containing trehalose and maltose and/or maltotriose. The characteristic means that the particulate composition containing crystalline trehalose dihydrate of the present invention is produced by a total sugar method, the particulate composition is different from a powder obtainable by simply mixing powdery products of trehalose and maltose and/or maltotriose.

The fact that the particulate composition of the present invention consists of particles containing trehalose and maltose and/or maltotriose can be confirmed by analyzing a saccharide composition of one particle contained in the particulate composition. Concretely, for example, it can be confirmed by the steps of collecting one particle of the particulate composition, dissolving into a small amount of water to make into a test solution and directly analyzing saccharides in the test solution by HPLC, or analyzing by HPLC after labeling the saccharides using a fluorescent reagent. In this case, the saccharide composition of the particle of the particulate composition is substantially the same with that of material saccharide solution. Even if each value of the saccharide composition is slightly different, the variation stays within the range of 1 to 2% as a value. The saccharide composition of one particle of the particulate composition can be confirmed by subjecting the particle to a high sensitivity analysis using a capillary electrophoresis apparatus.

Further, the second characteristic of the particulate composition containing crystalline trehalose dihydrate of the present invention is following (1):

(1) containing trehalose in an amount of 70% by weight or higher but 90% by weight or lower, on a dry solid basis.

The trehalose content is the same with that of material saccharide solution for the spray-drying. The above characteristic (1) means that the particulate composition containing crystalline trehalose dihydrate of the present invention is obtained by spray-drying a saccharide solution containing trehalose in an amount of 70 to 90% by weight, d.s.b. In other word, the above characteristic (1) means that the trehalose content of the saccharide solution for spray-drying is required to be in the range of 70 to 90% by weight, d.s.b., for producing the particulate composition containing crystalline trehalose dihydrate of the present invention.

Furthermore, the third characteristic of the particulate composition containing crystalline trehalose dihydrate of the present invention is following (2):

(2) containing maltose and/or maltotriose in a total amount of 3% by weight or higher, on a dry solid basis.

The total content of maltose and/or maltotriose is the same with that of material saccharide solution for the spray-drying. The above characteristic (2) means that the particulate composition containing crystalline trehalose dihydrate of the present invention is obtained by spray-drying a saccharide solution containing maltose and/or maltotriose in a total amount of 3% by weight or higher, d.s.b. In other word, the above characteristic (2) means that the total content of maltose and/or maltotriose of the saccharide solution for spray-drying is required to be 3% by weight or higher, d.s.b., for producing the particulate composition containing crystalline trehalose dihydrate of the present invention.

In addition, the fourth characteristic of the particulate composition containing crystalline trehalose dihydrate of the present invention is following (3):

(3) having a degree of crystallinity for crystalline trehalose dihydrate of 25% or higher but less than 90%, when calculated based on its powder X-ray diffraction profile.

The above characteristic (3) means that the particulate composition containing crystalline trehalose dihydrate of the present invention is obtained by converting a part of trehalose in amorphous form into crystalline trehalose dihydrate by aging. In other word, the above characteristic (3) means that the steps of spray-drying a saccharide solution containing trehalose and maltose and/or maltotriose in a prescribed ratio and aging the resulting dried particulate composition under prescribed conditions to give a degree of crystallinity for crystalline trehalose dihydrate of 25% or higher but less than 90%, are required for producing the particulate composition containing crystalline trehalose dihydrate of the present invention.

The reason is not certain why the particulate composition containing crystalline trehalose dihydrate, which consists of particles containing trehalose and maltose and/or maltotriose and has the above characteristics (1) to (3), has an extremely advantageous emulsifying ability in comparison with conventional particulate composition. However, it is presumed that the presence of trehalose in crystalline dihydrate form and amorphous form in a prescribed ratio in each particle which constitutes the particulate composition; and the presence of maltose and/or maltotriose in a mixed form in the particulate composition; are related to the advantageous emulsifying ability. Further, it is considered that the presence of maltose and/or maltotriose, as saccharides other than trehalose, in amorphous form in the particulate composition is related to the emulsifying ability of the particulate composition.

According to the confirmation by the inventors of the present invention, there are more preferable ranges in the content of each saccharide and the degree of crystallinity for crystalline trehalose dihydrate. Since the particulate composition containing crystalline trehalose dihydrate, which contains trehalose in an amount of 78% by weight or higher but 86% by weight or lower, d.s.b., and maltose and/or maltotriose in a total amount of 4% by weight or higher, d.s.b., and has the degree of crystallinity of 50% or higher but less than 90%, has more advantageous emulsifying ability, it can be more preferably used. In other word, the more preferable particulate composition containing crystalline trehalose dihydrate of the present invention has the following characteristics (1') to (3'):

(1') containing trehalose in an amount of 78% by weight or higher but 86% by weight or lower, d.s.b.;

(2') containing maltose and/or maltotriose in a total amount of 4% by weight or higher, d.s.b.; and (3') having a degree of crystallinity for crystalline trehalose dihydrate of 50% or higher but less than 90%, when calculated based on its powder X-ray diffraction profile.

The particulate composition containing crystalline trehalose dihydrate of the present invention, which consists of particles containing trehalose and maltose and/or maltotriose and has the above characteristics (1) to (3), has an advantageous emulsifying ability, and the numerous fine roughness is observed on the surface of particles constituting the particulate composition. The fifth characteristic of the particulate composition of the present invention is following (4):

(4) having a specific surface area of 0.25 $m^2/g$ or higher when determined by the gas adsorption isotherms using nitrogen.

Particularly, the particulate composition containing crystalline trehalose dihydrate, showing the value of emulsifying ability of 0.45 or higher, usually shows the specific surface area of 0.35 $m^2/g$ or higher. As described later in Experiment 3, the specific surface area of the conventional particulate composition is 0.18 $m^2/g$. Therefore, the particulate composition containing crystalline trehalose dihydrate of the present invention has a larger specific surface area than the conventional particulate composition and amorphous trehalose.

The particulate composition containing crystalline trehalose dihydrate of the present invention is not restricted to the one having a specific particle size distribution. Usually, the particulate composition having the following particle size distribution (5) is preferable:

(5) containing particles with a particle size of at least 53 μm but smaller than 300 μm in an amount of 50% by weight or higher based on the particulate composition as a whole, and particles with a particle size of smaller than 53 μm in an amount of 10% by weight or higher based on the particulate composition as a whole.

The particulate composition containing crystalline trehalose dihydrate of the present invention, having the particle size distribution of the above (5), can be more preferably used as the particulate composition having an emulsifying ability because the dispersability of the particulate composition into a liquid or powder is increased.

The particulate composition containing crystalline trehalose dihydrate of the present invention is characterized by its advantageous emulsifying ability. The particulate composition of the present invention is not restricted to the one having a specific emulsifying ability as far as it has higher emulsifying ability than the conventional particulate composition, but usually shows following characteristic (6):

(6) the turbidity at 720 nm of an emulsion is 0.35 or higher, more preferably, 0.45 or higher when the emulsion is prepared by the steps of mixing 5 parts by weight of said particulate composition and one part by weight of corn oil, admixing with 500 parts by weight of purified water, and stirring the mixture.

As described later, the value of the turbidity at 720 nm of an emulsion, prepared using conventional particulate composition by the same method, is low, about 0.10. The fact that the particulate composition of the present invention gives the value of the turbidity of 0.35 or higher indicates that the particulate composition of the present invention has an extremely advantageous emulsifying ability in comparison with the conventional composition. As far as the present inventor's knowledge, a particulate composition containing crystalline trehalose dihydrate, having such a high emulsifying ability, has not present before the present application.

3. Process for Producing the Particulate Composition Containing Crystalline Trehalose Dihydrate of the Present Invention The particulate composition containing crystalline trehalose dihydrate of the present invention is not restricted to the one produced by a specific process as far as it has the above characteristics (1) to (3). However, it can be suitably produced by the process containing the following steps (A) to (D):

(A) a step of preparing a saccharide solution containing trehalose in an amount of 70% by weight or higher but 90% by weight or lower, d.s.b., and maltose and/or maltotriose in a total amount of 3% by weight or higher, d.s.b.;

(B) a step of pulverizing said saccharide solution by spray-drying;

(C) a step of crystallizing trehalose to form crystalline trehalose dihydrate by aging the resulting pulverized saccharide under a relative humidity of 60% or higher for 7 days or longer; and (D) a step of drying the resulting particulate composition containing crystalline trehalose dihydrate.

The above steps (A) to (D) are subsequently explained below:

<Step (A) (Step of Forming a Saccharide Solution Containing Trehalose)>

This step is the one of preparing a saccharide solution containing trehalose in an amount of 70% by weight or higher but 90% by weight or lower, d.s.b., and maltose and/or maltotriose in a total amount of 3% by weight or higher, d.s.b. As far as the saccharide solution contains trehalose in an amount of 70% by weight or higher but 90% by weight or lower, d.s.b., and maltose and/or maltotriose in a total amount of 3% by weight or higher, d.s.b., the method for preparing the saccharide solution is not restricted to the specific one, and the solution can be arbitrary produced by, for example, the method of allowing α-glycosyltrehalose-forming enzyme and trehalose-releasing enzyme to act on liquefied starch, disclosed in Japanese Patent No. 3557235; the method of allowing a maltose-trehalose converting enzyme to act on maltose solution, disclosed in Japanese Patent No. 3633648, and the method of allowing maltose phosphorylase and trehalose phosphorylase to act on maltose solution, disclosed in Japanese Patent Kokoku No. 060998/1988. Further, the saccharide solution can be prepared by the method of dissolving trehalose and maltose and/or maltotriose in purified water. Particularly, the method of allowing α-glycosyltrehalose-forming enzyme and trehalose-releasing enzyme to act on liquefied starch together with starch-debranching enzyme and cyclomaltodextrin glucanotransferase can be preferably used because the objective trehalose-containing solution can be prepared by a consistent enzymatic reaction using starch as a material. When the trehalose content of the saccharide solution is lower than 70% by weight, the solution can be arbitrarily purified by chromatography to increase the trehalose content.

<Step (B) (Step of Pulverizing the Trehalose-Containing Saccharide Solution by a Spray-Drying)>

This step is the one of pulverizing the trehalose-containing saccharide solution by subjecting it to a spray-drying. Methods for spray-drying and their conditions are not restricted as far as the particulate composition containing crystalline trehalose dihydrate, having an advantageous emulsifying ability, can be produced. The trehalose-containing saccharide solution is atomized by using, for example, a rotary-atomizer system or nozzle system such as pressurizing nozzle and two fluid nozzle. By the atomizing, the surface area of unit volume of solid saccharides is increased by atomizing. The atomized saccharides can be pulverized by allowing to contact with hot air continuously under the conditions of, for example, inlet temperature of 120 to 200° C. and outlet temperature of 60 to 100° C., and drying instantaneously. Particularly, the rotary-atomizer system is preferable because the particulate composition with a relatively narrow particle size distribution and relatively high fluidity can be obtained. Also, the particulate composition can be arbitrarily obtained by the steps of admixing seed crystals with the trehalose-containing saccharide solution to make into a massecuites, in which a part of trehalose is crystallized to form crystalline trehalose dihydrate, and spray-drying the resulting massecuites. Since massecuites contains solids, the rotary-atomizer system is preferably used for spray-drying the massecuites.

<Step (C) (Step of Crystallizing Trehalose to Form Crystalline Trehalose Dihydrate)>

This step is the one of crystallizing trehalose to form crystalline trehalose dihydrate by aging trehalose-containing powder obtained in the above step (B) under a relative humidity of 60% or higher for 7 days (24 hours×7 days=168 hours). Conditions of the relative humidity of less than 60% is not preferable because crystallization of trehalose to form crystalline trehalose dihydrate is not promoted, a large part of the powder remains in the form of amorphous, the particulate composition with the objective emulsifying ability cannot be obtained by its relatively smooth surface and relatively small specific surface area. Although the aging period is varied depending on the aging conditions (temperature and humidity), when the aging period is shorter than 7 days, it is not preferable because the particulate composition with the objective emulsifying ability cannot be obtained by its relatively smooth surface and relatively small specific surface area. The temperature for the aging is not restricted to specific one as far as the particulate composition with an advantageous emulsifying ability can be produced, and preferably at 10 to 40° C.

<Step (D) (Step of Drying a Particulate Composition Containing Crystalline Trehalose Dihydrate)>

This step is the one of drying the particulate composition containing crystalline trehalose dihydrate, obtained in the above step (C) to make into a final product. The method for drying is not restricted to the specific one as far as the objective particulate composition can be obtained. For example, a fluid bed drying method, in which the moisture of the particulate composition is evaporated by allowing the particulate composition to float in the air at a temperature of 40 to 80° C., and a vacuum drying method, in which the moisture of the particulate composition is evaporated under a reduced pressure condition, can be preferably used.

In the process for producing the particulate composition containing crystalline trehalose dihydrate of the present invention, the preparation of a trehalose-containing saccharide solution containing trehalose in an amount of 78% by weight or higher but 86% by weight or lower, d.s.b., and maltose and/or maltotriose in a total amount of 4% by weight or higher, d.s.b., is more preferable in the step of preparing a trehalose-containing solution for producing the particulate composition with a more advantageous emulsifying ability.

4. Uses of a Particulate Composition Containing Crystalline Trehalose Dihydrate of the Present Invention The particulate composition containing crystalline trehalose dihydrate of the present invention can be used for emulsifying a hydrophobic substance by mixing with the hydrophobic substance and further admixing with water. Therefore, it can be advantageously used as an emulsifier for hydrophobic substances, for example, vegetable oils such as rapeseed oil, soy bean oil, corn oil, sunflower oil, sesame oil, safflower oil, cotton seed oil, olive oil, palm oil, peanut oil, coconut oil, cocoa butter, shea butter, margarine, shortening, etc.; animal fats and oils such as milk fat, beef tallow, lard, mutton tallow, horse fat, whale fat, rabbit fat, chicken fat, liver oil, etc.; saturated fatty acids such as lauric acid, myristic acid, palmitic acid, stearic acid, behenic acid, etc.; unsaturated fatty acids such as oleic acid, linoleic acid, α-linolenic acid, eicosapentaenoic acid, docosahexaenoic acid, etc.; and fat-soluble vitamins such as vitamin A, vitamin D, vitamin E, vitamin K, etc.

As described above, the particulate composition containing crystalline trehalose dihydrate of the present invention can be used alone as an emulsifier, and if necessary, can be used in combination with other emulsifiers such as lecithin, saponin, casein sodium, glycerin fatty acid ester, sorbitan fatty acid ester, propylene glycol fatty acid ester, sucrose fatty acid ester, oxyethylene fatty acid alcohol, sodium oleate, morpholine fatty acid salt, polyoxyethlene higher fatty acid alcohol, calcium stearoyl lactate, monoglyceride ammonium phosphate, alkyl polyoxyethlene ether, etc. If necessary, it can be advantageously used in combination with thickening stabilizer such as arabic gum, guar gum, tamarind gum, locust bean gum, carrageenan, pectin, carboxymethyl cellulose, xanthan gum, gellan gum, dextran, pullulan, etc.

The particulate composition containing crystalline trehalose dihydrate of the present invention has a relatively high dissolution rate in water and hardly forms lump of powder. Therefore, it can be used for dispersing trehalose in a food material homogeneously even in the case of directly mixing to materials having a relatively low moisture content, for example, such as dough and cream. Accordingly, in the case of incorporating trehalose into the materials, a step of preliminary dissolving trehalose in water, which is essential in the case of conventional particulate composition containing crystalline trehalose dihydrate, can be omitted. Therefore, the particulate composition of the present invention can be preferably used for producing foods, cosmetics, quasi-drugs, and pharmaceuticals, having a relatively low moisture content.

The particulate composition containing crystalline trehalose dihydrate of the present invention can be used for the same use with the conventional particulate composition containing crystalline trehalose dihydrate. For example, it can be arbitrarily used for the production of foods and beverages such as Japanese confectionery, western confectionery, snack food, ice confection, retort food, frozen food, instant food, pickles, Tsukudani, paste product, dairy product, liquid food, baby food, healthy food, soft drink, carbonated drink, fruit juice drink, vegetable juice, milk beverage, coffee, tea drink, oolong tea, green tea drink, barley tea drink, alcoholic beverage, etc.; cosmetics such as face lotion, essence, emulsion, cream, foundation, mascara, lipstick, manicure, cleansing, facial wash, mouth wash, shampoo, treatment, conditioner, hair dressing, perfume, etc.; quasi-drugs and pharmaceuticals.

The following experiments explain the present invention in detail:

Experiment 1: Comparison of Emulsifying Abilities of Particulate Compositions Comprising Crystalline Trehalose Dihydrate, Prepared from Saccharide Solutions with Various Trehalose Contents In order to investigate the effect of a trehalose content on the emulsifying ability of a particulate composition containing crystalline trehalose dihydrate, various saccharide solutions different in trehalose contents were prepared, and particulate compositions containing crystalline trehalose dihydrate were produced from the respective saccharide solution by spray-drying method. Successively, the emulsifying abilities of those were determined.

Corn starch was suspended in purified water to give a solid concentration of 33% by weight, admixed with calcium chloride to give a solid concentration of 0.1% by weight, and then adjusted to pH 6.0 to make into a starch suspension. The starch suspension was admixed with "SPI-TASE HK", a product name of a thermostable α-amylase specimen commercialized by Nagase ChemteX Corporation, Osaka, Japan, in an amount of 10 units/g, d.s.b., and hydrolyzed at 100° C. for 30 min by passing through a continuous liquefier at a flow rate of 1 L/min, and then heated at 140° C. for 5 min to stop the reaction to make into a liquefied starch solution. The resulting liquefied starch solution was cooled to 50° C., admixed with an enzyme specimen containing an α-glycosyltrehalose-forming enzyme and trehalose-releasing enzyme, prepared by the method described in Experiment 1-1 of International Publication No. WO2013/042587, to give enzyme amounts of 2 units/g-starch of the α-glycosyltrehalose-forming enzyme and 10 units/g-starch of the trehalose-releasing enzyme; and further admixed with 300 units/g-starch of an isoamylase specimen commercialized by Hayashibara Co., Ltd., Okayama, Japan, and 2 units/g-starch of CGTase derived from *Paenibacillus illinoisensis* NBRC15959, prepared by the method described in Experiment1-2 of International Publication No. WO2013/042587 and enzymatically reacted for 11 hours. Successively, the reaction mixture was admixed with 10 units/g-starch of "NEOSPITASE PK-2", an α-amylase specimen commercialized by Nagase ChemteX Corporation, Osaka, Japan, enzymatically reacted at 80° C. for 2 hours, and heated at 100° C. for 30 min to stop the enzyme reaction to make into a saccharified solution. The resulting saccharified solution was decolored by using activated charcoal, deionized using ion-exchange resins, and concentrated to give a solid concentration of 30% by weight. By the above method, Trehalose-containing saccharide solution 1, having a saccharide composition shown in Table 1 was obtained.

Trehalose-containing saccharide solution 5 having a saccharide composition shown in Table 1, with a solid concentration 30% by weight, was obtained by the same method described above except for allowing α-glycosyltrehalose-forming enzyme, trehalose-releasing enzyme, isoamylase, and CGTase to act on liquefied starch solution for 48 hours in the process of trehalose-forming reaction.

While, Trehalose-containing saccharide solution 9 having a saccharide composition shown in Table 1, with a solid concentration 30% by weight, was obtained by dissolving "TREHA (B/FUN)", a product name of commercialized particulate composition containing crystalline trehalose dihydrate, commercialized by Hayashibara Co., Ltd., Okayama, Japan, in a purified water to give a solid concentration of 30% by weight.

Successively, Trehalose-containing saccharide solutions 2 to 4, having saccharide compositions shown in Table 1, were respectively prepared by mixing Trehalose-containing saccharide solutions 1 and 5 in various prescribed ratios. Further, Trehalose-containing saccharide solutions 6 to 8, having saccharide compositions shown in Table 1, were respectively prepared by mixing Trehalose-containing solutions 5 and 9 in various prescribed ratios.

TABLE 1

| Trehalose-containing saccharide solution | Saccharide composition (% by weight) | | | | |
|---|---|---|---|---|---|
| | Trehalose | Glucose | Maltose | Maltotriose | Other saccharides |
| 1 | 64.3 | 1.6 | 3.5 | 3.8 | 26.8 |
| 2 | 73.8 | 2.7 | 3.2 | 2.8 | 17.5 |
| 3 | 77.5 | 3.1 | 3.1 | 2.4 | 13.9 |
| 4 | 80.9 | 3.5 | 3.0 | 2.0 | 10.6 |
| 5 | 85.7 | 4.0 | 2.9 | 1.5 | 5.9 |
| 6 | 88.1 | 3.4 | 2.4 | 1.3 | 4.9 |
| 7 | 93.0 | 2.1 | 1.4 | 0.8 | 2.8 |
| 8 | 97.7 | 0.8 | 0.4 | 0.3 | 0.7 |
| 9 | 99.2 | 0.4 | 0.1 | 0.2 | 0.1 |

The particulate composition, Samples 1 to 9, varying in trehalose content, were respectively obtained by the steps of spray-drying Trehalose-containing saccharide solutions 1 to 9, with a solid concentration of 30% by weight, prepared above, under the conditions of inlet temperature of 180° C., outlet temperature of 90° C., and feeding speed of 2 L/hour by using a spray-dryer with rotary-atomizer system. Then, Samples 1 to 9 were aged under the conditions at a temperature of 25° C. and either of a high relative humidity of 75% or 90%. In the course of aging, a part of each sample was withdrawn at the time points of just before aging, aged for one day, aged for 5 days, and aged for 7 days. Each sample, withdrawn above, was dried in vacuo at 25° C. for 18 hours, and the emulsifying ability was measured by the aforesaid method. Each sample, aged for 7 days, was subjected to the measurement of the degree of crystallinity for crystalline trehalose dihydrate. In this experiment, "TREHA B/FUN", a conventional particulate composition containing crystalline trehalose dihydrate, commercialized by Hayashibara Co., Ltd., Okayama, Japan, which is produced by the conventional crystallizing method, i.e., method of crystallizing and separating crystals from molasses, was used as control. The results are shown in Table 2. In the table, a sample showing the value of emulsifying ability of 0.35 or higher and that showing the value of emulsifying ability of 0.45 or higher were indicated by symbols, "*" and "**", respectively.

TABLE 2

| Sample (Particulate composition) | Trehalose Content (% by wt) | Before aging | Emulsifying ability (Absorbance at 720 nm) | | | | | | Degree of crystallinity*** of the composition aged for 7 days | |
|---|---|---|---|---|---|---|---|---|---|---|
| | | | Aged for 1 day | | Aged for 5 days | | Aged for 7 days | | | |
| | | — | RH75 | RH90 | RH75 | RH90 | RH75 | RH90 | RH75 | RH90 |
| 1 | 64.3 | 0.10 | 0.15 | 0.11 | 0.07 | 0.23 | 0.22 | 0.27 | 4.6 | 20.4 |
| 2 | 73.8 | 0.09 | 0.11 | 0.10 | 0.07 | 0.06 | 0.40* | 0.47** | 29.5 | 48.8 |
| 3 | 77.5 | 0.07 | 0.14 | 0.09 | 0.25 | 0.32 | 0.47** | 0.45** | 56.1 | 61.1 |
| 4 | 80.9 | 0.06 | 0.14 | 0.14 | 0.08 | 0.18 | 0.52** | 0.46** | 59.5 | 59.3 |
| 5 | 85.7 | 0.05 | 0.11 | 0.05 | 0.10 | 0.30 | 0.48** | 0.49** | 55.7 | 60.2 |
| 6 | 88.1 | 0.04 | 0.11 | 0.06 | 0.31 | 0.20 | 0.39* | 0.41* | 53.6 | 66.4 |
| 7 | 93.0 | 0.05 | 0.07 | 0.10 | 0.13 | 0.19 | 0.26 | 0.26 | 77.1 | 74.5 |
| 8 | 97.7 | 0.04 | 0.11 | 0.05 | 0.14 | 0.16 | 0.14 | 0.17 | 84.5 | 86.1 |
| 9 | 99.2 | 0.05 | 0.06 | 0.06 | 0.14 | 0.13 | 0.12 | 0.15 | 84.6 | 89.3 |
| Control | 99.2 | | | | 0.10 | | | | 89.6 | |

RH: Relative humidity (%),
wt: weight
***Degree of crystallinity for crystalline trehalose dihydrate As shown in Table 2, in the cases of Sample 1 with a trehalose content of 64.3% by weight, and Samples 7 to 9, with trehalose contents of 93.0% by weight or higher, those values of emulsifying ability showed no increase even after the aging step, and the values were in the range of 0.12 to 0.27, and revealed no significant difference from the value, 0.10, of the control particulate composition. On the other hand, in the cases of Samples 2 to 6, with trehalose contents in a range of 73.8 to 88.1% by weight, d.s.b., the values of emulsifying ability increased during the aging step and showed significantly high values, 0.39 to 0.52, after aging for 7 days. Particularly, in the cases of Samples 3 to 5, with trehalose contents in a range of 77.5 to 85.7% by weight, d.s.b., they showed significantly high values, 0.45 to 0.52, after aging for 7 days. The values of emulsifying ability of Samples 1 to 9 showed no significant change after aging for 7 days.

As also shown in Table 2, Samples 2 to 6, showing the values of emulsifying ability of 0.35 or higher, showed degrees of crystallinity for crystalline trehalose dihydrate of 29.5% or higher, particularly, Samples 3 to 5, showing the values of emulsifying ability of 0.45 or higher, showed degrees of crystallinity for crystalline trehalose dihydrate of 56.1% or higher. In the powder X-ray diffraction profiles of Samples 1 to 9, no diffraction peak other than diffraction peaks derived from crystalline trehalose dihydrate was detected. Accordingly, it was revealed that Samples 1 to 9 did not substantially contain crystals other than crystalline trehalose dihydrate.

These results indicate that the particulate composition containing crystalline trehalose dihydrate, prepared by the steps of spray-drying a trehalose-containing saccharide solution with a trehalose content of 70% by weight or higher but 90% by weight or lower, aging the resulting powder for 7 days or longer to increase the degree of crystallinity for crystalline trehalose dihydrate to 25% or higher, has an advantageous emulsifying ability, particularly, these results indicate that the particulate composition containing crystalline trehalose dihydrate, prepared by the steps of spray-drying a trehalose-containing saccharide solution with a trehalose content of 78% by weight or higher but 86% by weight or lower, aging the resulting powder for 7 days or longer to increase the degree of crystallinity for crystalline trehalose dihydrate to 50% or higher, has an more advantageous emulsifying ability.

Experiment 1-2: Effect of Saccharides Other than Trehalose on the Emulsifying Ability of the Particulate Composition Containing Crystalline Trehalose Dihydrate Successively, in order to investigate the effect of saccharides other than trehalose on the emulsifying ability of the particulate composition containing crystalline trehalose dihydrate, various trehalose-containing saccharide solution, containing trehalose together with glucose, maltose, maltotriose, sorbitol, or maltitol, were prepared and made into particulate compositions containing crystalline trehalose dihydrate by spray-drying method, and then the emulsifying abilities of the particulate compositions were measured.

Trehalose and either of glucose (commercialized by FUJIFILM Wako Pure Chemical Corporation, Osaka, Japan), maltose ("MALTOSE 999", commercialized by Hayashibara Co., Ltd., Okayama, Japan), maltotriose ("MALTOTRIOSE", commercialized by Hayashibara Co., Ltd., Okayama, Japan), sorbitol (commercialized by FUJIFILM Wako Pure Chemical Corporation, Osaka, Japan), or maltitol (commercialized by FUJIFILM Wako Pure Chemical Corporation, Osaka, Japan) were dissolved in water to give a solid concentration of 30% by weight, trehalose content of 85% by weight, d.s.b., and other saccharide content of 15% by weight, d.s.b. to make into trehalose-containing saccharide solution, and then resulting solution was spray-dried by the same method in Experiment 1-1 to make into a powder. Successively, the resulting powder was aged at 25° C. under a relative humidity of 75% for 7 days, and dried in vacuo at 25° C. for 18 hours to make into particulate compositions, Samples A to E, containing either glucose, maltose maltotriose, sorbitol, or maltitol as a concomitant saccharide, respectively. Then, the emulsifying abilities and degrees of crystallinity for crystalline trehalose dihydrate of Samples A to E were measured using aforesaid methods. In this experiment, the particulate composition, Samples F to H, which were prepared by simply mixing "TREHALOSE 999", a reagent grade particulate composition containing crystalline trehalose dihydrate, commercialized by Hayashibara Co. Ltd., Okayama, Japan, and either of "MALTOSE 999", a reagent grade crystalline β-maltose monohydrate powder, commercialized by Hayashibara Co. Ltd., Okayama, Japan; an amorphous maltose powder, which is prepared by the same method of "a powdered standard sample containing trehalose, where the powdered standard sample consists substantially of an amorphous form of trehalose" described above); or "MALTOTRIOSE", an amorphous maltotriose powder, commercialized by Hayashibara Co. Ltd., Okayama, Japan; to give a trehalose content of 85% by weight, d.s.b., and the content of a saccharide than trehalose of 15% by weight, d.s.b., and then those emulsifying abilities were measured. The results are shown in Table 3.

TABLE 3

| Sample (Particulate Composition) | | Saccharide composition (on a dry solid basis) | | Degree of crystallinity for crystalline trehalose dihydrate (%) | Emulsifying ability (Absorbance at 720 nm) |
|---|---|---|---|---|---|
| | | 85% by weight | 15% by weight | | |
| Spray-drying + Aging | A | Trehalose | Glucose | 86.6 | 0.09 |
| | B | | Maltose | 86.1 | 0.46 |
| | C | | Maltotriose | 70.6 | 0.47 |
| | D | | Sorbitol | 74.4 | 0.10 |
| | E | | Maltitol | 71.3 | 0.16 |
| Mixing | F | Particulate composition containing crystalline trehalose dihydrate | Crystalline β-maltose monohydrate powder | 100* | 0.05 |
| | G | | Amorphous maltose powder | 100* | 0.06 |
| | H | | Amorphous maltotriose powder | 100* | 0.06 |

*Degree of crystallinity of a particulate composition containing crystalline trehalose dihydrate, used for mixing.

As shown in Table 3, Samples A and B, obtained by the steps of spray-drying trehalose-containing saccharide solution, which contains glucose or maltose as a concomitant saccharide, and aging the resultant, showed almost equal degrees of crystallinity of 86.1 to 86.6%. However, Sample A showed substantially no emulsifying ability, while Sample B showed an extremely high value of emulsifying ability of 0.46. On the other hand, Samples C to E, obtained by the steps of spray-drying trehalose-containing saccharide solution, which contains maltotriose, sorbitol, or maltitol as a concomitant saccharide, and aging the resultant, showed almost equal degrees of crystallinity of 70.6 to 74.4%. However, Samples D and E showed substantially no emulsifying ability, while Sample C showed an extremely high value of emulsifying ability of 0.47. Since Samples A to E showed no diffraction peak other than those originated from crystalline trehalose dihydrate in their powder X-ray diffraction profiles, it was confirmed that those samples do not substantially contain crystals other than crystalline trehalose dihydrate.

Also as shown in Table 3, Samples F to H, produced by simply mixing a particulate composition containing crystalline trehalose dihydrate and crystalline β-maltose monohydrate powder, amorphous maltose powder, or amorphous maltotriose powder, showed substantially no emulsifying ability. On the contrary, Samples B and C, obtained by the steps of spray-drying a trehalose-containing saccharide solution containing maltose or maltotriose as concomitant saccharides and aging the resultant, showed remarkably high values for emulsifying ability of 0.46 and 0.47, respectively. It was considered that powdered respective particles reflect the saccharide composition of the material saccharide solution based on the principle of spray-drying of spraying the material saccharide solution to make into fine particles and pulverizing them by drying instantaneously. Therefore, it was considered that the powder obtained by the spray-drying composed of particles containing trehalose and maltose and/or maltotriose. Further, it was considered that, in the respective powder particle, trehalose in crystalline trehalose dihydrate form and in amorphous form were present in a mixed form because a part of trehalose in the powder is converted from amorphous form into crystalline dihydrate form during aging. In other words, powders obtained by the steps of spray-drying trehalose-containing saccharide solution and aging the resultant were different from powders prepared by simply admixing maltose powder and/or maltotriose powder with conventional particulate composition containing crystalline trehalose dihydrate in the following two points:

(1) Trehalose in the form of crystalline dihydrate and that in the form of amorphous are present in a prescribed ratio in the respective particle; and
(2) Maltose and maltotriose in amorphous forms are also present in the respective particle in a mixed form.

Therefore, it was considered that the existing form as the powder is important for exhibiting the emulsifying ability.

These results indicate that, in the case of the particulate composition containing crystalline trehalose dihydrate, the emulsifying ability of the particulate composition varies depending on the concomitant saccharides and their existing form even though particulate compositions are in equal level in trehalose content and degree of crystallinity for crystalline trehalose dihydrate. The results also indicate that a particulate composition containing crystalline trehalose dihydrate, having a satisfactory emulsifying ability, can not be produced by simple mixing of particulate composition containing crystalline trehalose dihydrate and other saccharide components, and that a particulate composition containing crystalline trehalose dihydrate, having a satisfactory emulsifying ability, can be obtained only when a trehalose-containing saccharide solution that also contains maltose and/or maltotriose as concomitant saccharides is spray-dried and aged to obtain a particulate composition comprising crystalline trehalose dihydrate composed of the particles containing trehalose and maltose and/or maltotriose in a specified ratio.

Although concrete data were omitted, about 0.3 mg/particle of five powder particles were respectively collected from above Sample B with tweezers, dissolved in 25 µL of purified water, and subjected to the aforesaid HPLC analysis for determining the saccharide composition. As the results, each of the particles showed substantially same saccharide composition, i.e., the trehalose content of 85±1% by weight and maltose content of 15±1% by weight. Also in the case of the above Sample F prepared by simply mixing a particulate composition containing crystalline trehalose dihydrate and crystalline maltose monohydrate powder, the saccharide compositions of five powder particles were determined and it was revealed that either the particles with trehalose content of 99.9% by weight or those with maltose content of 99.9% by weight were detected. The results indicate that the particulate composition containing comprising crystalline trehalose dihydrate of the present invention can be clearly distinguished from a simple mixture of commercially available particulate composition containing crystalline trehalose dihydrate and maltose-containing powder.

Since it was revealed from the results in Experiment 1-2 that, in order to produce a particulate composition containing crystalline trehalose dihydrate having an emulsifying ability, the steps of spray-drying a trehalose-containing saccharide solution containing maltose and/or maltotriose as concomitant saccharides and aging the resultant were important, the results for Samples 2 to 6, Sample B, and Sample C, which were particulate compositions containing crystalline trehalose dihydrate, having satisfactory emulsifying abilities, prepared in Experiments 1-1 and 1-2, are rearranged from the view point of the total content of maltose and maltotriose, and are shown in Table 4.

TABLE 4

| Sample (Particulate composition) No. | Trehalose content (% by weight) | Total content of maltose and maltotriose (% by weight) | Degree of crystallinity for crystalline trehalose dihydrate (%) | | Emulsifying ability (Absorbance at 720 nm) | |
|---|---|---|---|---|---|---|
| | | | RH75 | RH90 | RH75 | RH90 |
| 2 | 73.8 | 6.0 | 29.5 | 48.8 | 0.40* | 0.47** |
| 3 | 77.5 | 5.5 | 56.1 | 61.1 | 0.47** | 0.45** |
| 4 | 80.9 | 5.0 | 59.5 | 59.3 | 0.52** | 0.46** |

TABLE 4-continued

| Sample (Particulate composition) No. | Trehalose content (% by weight) | Total content of maltose and maltotriose (% by weight) | Degree of crystallinity for crystalline trehalose dihydrate (%) | | Emulsifying ability (Absorbance at 720 nm) | |
|---|---|---|---|---|---|---|
| | | | RH75 | RH90 | RH75 | RH90 |
| 5 | 85.7 | 4.4 | 55.7 | 60.2 | 0.48** | 0.49** |
| 6 | 88.1 | 3.7 | 53.6 | 66.4 | 0.39* | 0.41* |
| B | 85.0 | 15.0 | 86.1 | | 0.46** | |
| C | 85.0 | 15.0 | 70.6 | | 0.47** | |

RH: Relative humidity (%)

As shown in Table 4, Samples 2 to 6, Sample B, and Sample C, which showed the values for emulsifying ability of 0.35 or higher, had the total content of maltose and maltotriose of 3.7% by weight or higher, and trehalose content in a range of 73.8% by weight or higher but 88.1% by weight or lower, and the degree of crystallinity in a range of 29.5% or higher but 86.1% or lower. Particularly, Samples 3 to 5, which showed the values for emulsifying ability of 0.45 or higher, had the total content of maltose and maltotriose of 4.4% by weight or higher, and trehalose content in a range of 77.5% by weight or higher but 85.7% by weight or lower, and the degree of crystallinity in a range of 56.1% or higher but 86.1% or lower. While, although not shown in Table 4, it was revealed from Table 2 that Samples 7 to 9, which showed the low-values for emulsifying ability of 0.26 or lower, had a high trehalose content of 93.0% by weight or higher and the total content of maltose and maltotriose of less than 3% by weight, and the degree of crystallinity in a range of 74.5 to 89.3%. The reason why the emulsifying abilities of Sample 7 to 9 are low even though the degrees of crystallinity are equivalent to other samples was inferred that maltose contents and maltotriose contents of those sample were relatively low.

Judging comprehensively from the findings obtained in Experiments 1-1 and 1-2, it was revealed that a particulate composition containing crystalline trehalose dihydrate, which contains trehalose in an amount of 70% by weight or higher but 90% by weight or lower, d.s.b., and maltose and/or maltotriose in a total amount of 3% by weight or higher, d.s.b., and has a degree of crystallinity for crystalline trehalose dihydrate of 25% or higher but less than 90%, exhibited the emulsifying ability of 0.35 or higher. Particularly, it was revealed that a particulate composition containing crystalline trehalose dihydrate, which contains trehalose in an amount of 78% by weight or higher but 86% by weight or lower, d.s.b., and maltose and/or maltotriose in a total amount of 4% by weight or higher, d.s.b., and has a degree of crystallinity for crystalline trehalose dihydrate of 50% or higher but less than 90%, exhibited the emulsifying ability of 0.45 or higher.

Experiment 2: Observation of Surface of the Particulate Composition Containing Crystalline Trehalose Dihydrate Using a Scanning Electron Microscope In order to clarify the structural difference between the particulate composition containing crystalline trehalose dihydrate, having an advantageous emulsifying ability, and that having no substantial emulsifying ability, the surfaces of the particles composing the particulate compositions were observed using a scanning electron microscope.

The surfaces of Sample 1, 3, 4, 5, and 9, obtained by aging under a relative humidity of 75% for 7 days in Experiment 1-1, were observed using "SU3500", a scanning electron microscope commercialized by Hitachi High-Technologies Corporation, Tokyo, Japan, and the results were shown in FIGS. 1 to 5, respectively.

Figure 2:
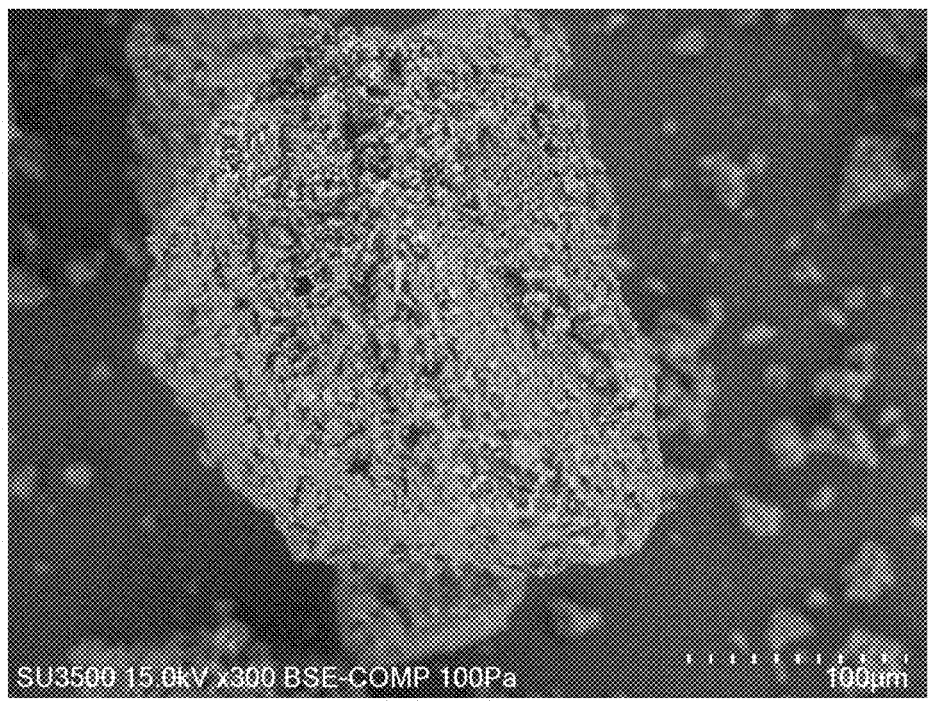
FIG. 2 is a photograph (300-fold magnification) of scanning electron microscope of Sample 3, a particulate composition containing crystalline trehalose dihydrate, obtained in Example 1-1 (which was aged under a relative humidity of 75% for 7 days).
Figure 3:
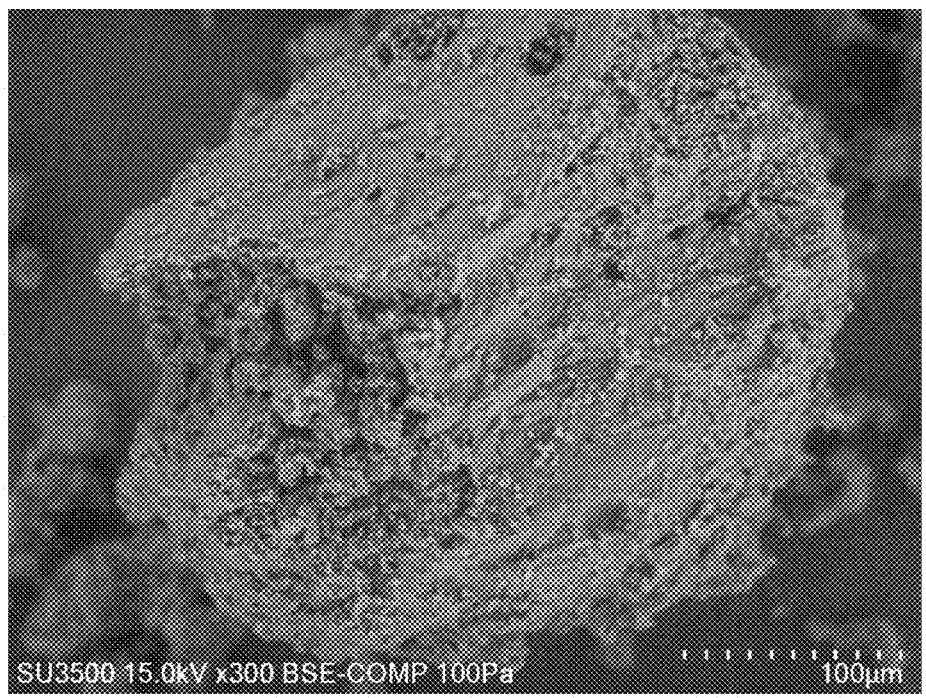
FIG. 3 is a photograph (300-fold magnification) of scanning electron microscope of Sample 4, a particulate composition containing crystalline trehalose dihydrate, obtained in Example 1-1 (which was aged under a relative humidity of 75% for 7 days).
Figure 4:
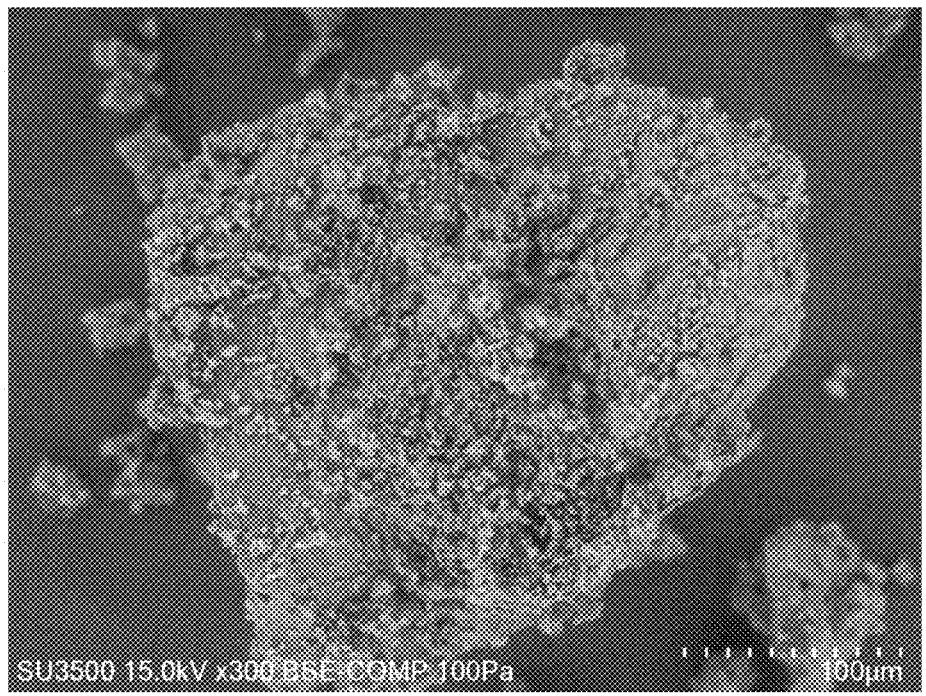
FIG. 4 is a photograph (300-fold magnification) of scanning electron microscope of Sample 5, a particulate composition containing crystalline trehalose dihydrate, obtained in Example 1-1 (which was aged under a relative humidity of 75% for 7 days).
Figure 5:
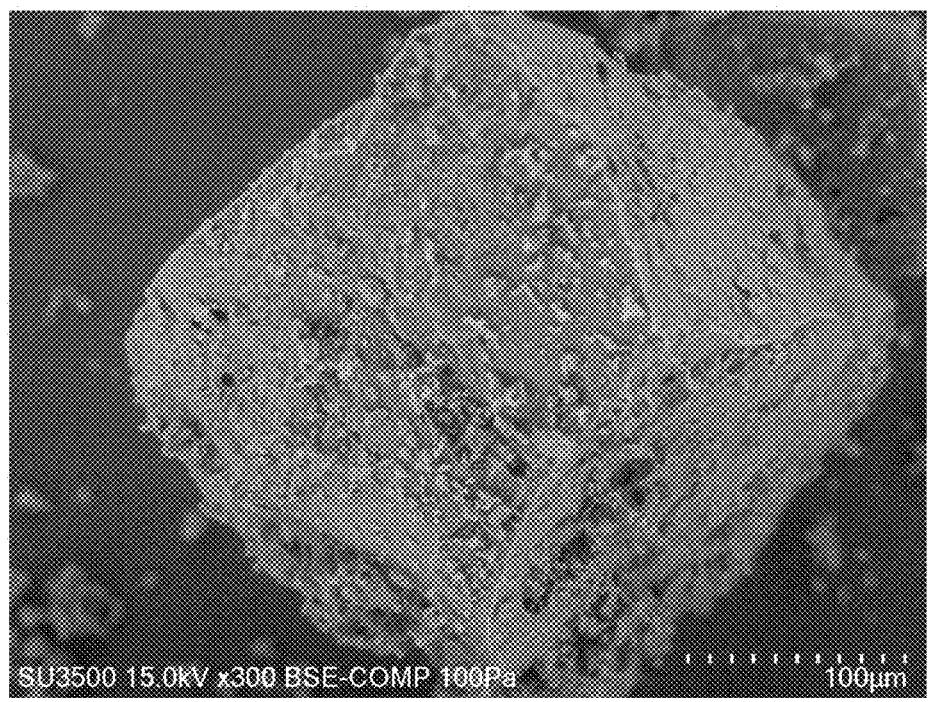
FIG. 5 is a photograph (300-fold magnification) of scanning electron microscope of Sample 9, a particulate composition containing crystalline trehalose dihydrate, obtained in Example 1-1 (which was aged under a relative humidity of 75% for 7 days).

As shown in FIGS. 1 and 5, Samples 1 and 9 showed relatively smooth surfaces. While, as shown in FIGS. 2 to 4, Samples 3 to 5 showed numerous fine roughness on the surface. Since Sample 1 showed a low degree of crystallinity for crystalline trehalose dihydrate of 4.6% and the large part of the particulate composition remained in an amorphous form, it was considered that Sample 1 was formed to be a particulate composition with a smooth surface. Since Sample 9 showed a high degree of crystallinity for crystalline trehalose dihydrate of 84.6% and the large part of the particulate composition was converted into crystalline form, it was considered that Sample 9 was formed to be a particulate composition with a smooth surface. On the other hand, since Samples 3 to 5 showed a degree of crystallinity for crystalline trehalose dihydrate of 55.7 to 59.5% and contained amorphous and crystal moderately, it was considered that they were formed to be a particulate composition having a rough surface. These results suggest that a particulate composition with a rough surface has an advantageous emulsifying ability.

Experiment 3: Measurement of the Specific Surface Area of the Particulate Composition Containing Crystalline Trehalose Dihydrate Since numerous fine roughness were observed on the surface of the particulate composition containing crystalline trehalose dihydrate with an advantageous emulsifying ability in comparison with that showing substantially no emulsifying ability, the specific surface area of the particulate composition containing crystalline trehalose dihydrate with an advantageous emulsifying ability was measured.

The surface areas of Samples 2 to 6, obtained by aging under a relative humidity of 75% for 7 days in Experiment 1-1, were measured by the aforesaid method. "TREHA B/FUN (pulverized)", a conventional particulate composition containing crystalline trehalose dihydrate commercialized by Hayashibara Co., Ltd., Okayama, Japan, was used as a control. The results are shown in Table 5.

TABLE 5

| Sample (Particulate Composition) No. | Trehalose content (% by weight) | Emulsifying ability (Absorbance at 720 nm) | Specific surface area ($m^2/g$) |
|---|---|---|---|
| 2 | 73.8 | 0.40 | 0.26 |
| 3 | 77.5 | 0.47 | 0.36 |
| 4 | 80.9 | 0.52 | 0.40 |
| 5 | 85.7 | 0.48 | 0.61 |
| 6 | 88.1 | 0.39 | 0.50 |
| Control | 99.2 | 0.10 | 0.18 |

As is evident from Table 5, the specific surface area of the control particulate composition, showing substantially no emulsifying ability, was 0.18 m$^2$/g. While, the specific surface areas of Sample 2 to 6, showing the values of emulsifying ability of 0.35 or higher, were 0.26 to 0.61 m$^2$/g. Particularly, the specific surface areas of Sample 3 to 5, showing the values of emulsifying ability of 0.45 or higher, were 0.36 to 0.61 m$^2$/g. Although there is no strict correlation between the value of emulsifying ability and the specific surface area, these results indicate that the particulate composition containing crystalline trehalose dihydrate, showing the value of emulsifying ability of 0.35 or higher, has the specific surface area of 0.25 m$^2$/g or higher, and that showing the value of emulsifying ability of 0.45 or higher, has the specific surface area of 0.35 m$^2$/g or higher.

The present invention will be explained in more detail based on the following Examples but it should never be restricted thereby.

Example 1

Particulate Composition Containing Crystalline Trehalose Dihydrate

A trehalose solution with a solid concentration of 30% (w/v), containing 85.7% by weight, d.s.b., of trehalose, 2.9% by weight, d.s.b. of maltose, and 1.5% by weight, d.s.b., of maltotriose, was prepared by the same method in Experiment 1-1. The resulting trehalose solution was subjected to spray-drying using "L-8 model Spray-Dryer", a spray-dryer commercialized by Ohkawara Kakohki Co., Ltd., Kanagawa, Japan. The spray-drying was carried out by an atomizer-system with conditions of inlet temperature of 180° C., outlet temperature of 90° C., and feeding speed of 2 L/hour. The resulting powder was aged at a temperature of 25° C. under a relative humidity of 60% for 7 days, and successively dried in vacuo at 25° C. for 18 hours to make into a particulate composition containing crystalline trehalose dihydrate.

The emulsifying ability, degree of crystallinity for crystalline trehalose dihydrate, and specific surface area of the product were determined to be 0.51, 46.9%, and 0.61 m$^2$/g, respectively. The product was subjected to a particle size distribution measurement and was revealed that it contained particles with a particle size of at least 53 μm but smaller than 300 μm in an amount of 60% by weight based on the particulate composition as a whole, and particles with a particle size of smaller than 53 μm in an amount of 20% by weight based on the particulate composition as a whole. One particle (about 0.3 mg) of the product was collected by using a tweezers, dissolved in 25 μL of purified water, and the resulting solution was subjected to a conventional HPLC analysis to determine the saccharide composition. By the analysis, it was revealed that the particle showed the same saccharide composition with aforesaid trehalose solution used as a material of spray-drying. Since the product has an advantageous emulsifying ability, it can be advantageously used for the production of, particularly, foods and cosmetics, rich in fats and oils. The product can be arbitrary used as a material for foods and cosmetics as in the cases of conventional particulate compositions containing crystalline trehalose dihydrate.

Example 2

<Particulate Composition Containing Crystalline Trehalose Dihydrate>

A trehalose solution with a solid concentration of 30% (w/v), containing 80.9% by weight, d.s.b., of trehalose, 3.0% by weight, d.s.b. of maltose, and 2.3% by weight, d.s.b., of maltotriose, was prepared by the same method in Experiment 1-1. The resulting trehalose solution was subjected to spray-drying using "L-8 model Spray-Dryer", a spray-dryer commercialized by Ohkawara Kakohki Co., Ltd., Kanagawa, Japan. The spray-drying was carried out by an atomizer-system with conditions of inlet temperature of 180° C., outlet temperature of 90° C., and feeding speed of 2 L/hour. The resulting powder was aged at a temperature of 20° C. in a relative humidity of 60% for seven days, and successively dried in vacuo at 25° C. for 18 hours to make into a particulate composition containing crystalline trehalose dihydrate.

The emulsifying ability, degree of crystallinity for crystalline trehalose dihydrate, and specific surface area of the product were determined to be 0.46, 43.2%, and 0.49 m$^2$/g, respectively. The product was subjected to a particle size distribution measurement and was revealed that it contained particles with a particle size of at least 53 μm but smaller than 300 μm in an amount of 62% by weight based on the particulate composition as a whole, and particles with a particle size of smaller than 53 μm in an amount of 18% by weight based on the particulate composition as a whole. Since the product has an advantageous emulsifying ability, it can be advantageously used for the production of, particularly, foods and cosmetics, rich in fats and oils. The product can be arbitrary used as a material for foods and cosmetics as in the cases of conventional particulate composition containing crystalline trehalose dihydrate.

Example 3

<Particulate Composition Containing Crystalline Trehalose Dihydrate>

A trehalose solution with a solid concentration of 30% (w/v), containing 73.7% by weight, d.s.b., of trehalose, 3.5% by weight, d.s.b. of maltose, and 3.4% by weight, d.s.b., of maltotriose, was prepared by the same method in Experiment 1-1. The resulting trehalose solution was subjected to spray-drying using "L-8 model Spray-Dryer", a spray-dryer commercialized by Ohkawara Kakohki Co., Ltd., Kanagawa, Japan. The spray-drying was carried out by an atomizer-system with conditions of inlet temperature of 180° C., outlet temperature of 90° C., and feeding speed of 2 L/hour. The resulting powder was aged at a temperature of 20° C. in a relative humidity of 60% for seven days, and successively dried in vacuo at 25° C. for 18 hours to make into a particulate composition containing crystalline trehalose dihydrate.

The emulsifying ability, degree of crystallinity for crystalline trehalose dihydrate, and specific surface area of the product were determined to be 0.43, 32.8%, and 0.30 m$^2$/g, respectively. The product was subjected to a particle size distribution measurement and was revealed that it contained particles with a particle size of at least 53 μm but smaller than 300 μm in an amount of 65% by weight based on the particulate composition as a whole, and particles with a particle size of smaller than 53 μm in an amount of 12% by weight based on the particulate composition as a whole. Since the product has an advantageous emulsifying ability, it can be advantageously used for the production of, particularly, foods and cosmetics, rich in fats and oils. The product can be arbitrary used as a material for foods and cosmetics as in the cases of conventional particulate composition containing crystalline trehalose dihydrate.

Example 4

<Particulate Composition Containing Crystalline Trehalose Dihydrate>

A trehalose solution containing 85.2% by weight, d.s.b., of trehalose, 3.0% by weight, d.s.b. of maltose, and 1.8% by weight, d.s.b., of maltotriose, was prepared by the same method in Experiment 1-1, and then concentrated to give a solid concentration of 70% (w/v). To the resulting trehalose solution, 2% by weight, d.s.b., of crystalline trehalose dihydrate was added as seed crystals and the resulting solution was kept at room temperature for 12 hours to prepare massecuites, and the resulting massecuites was subjected to spray-drying using "L-8 model Spray-Dryer", a spray-dryer commercialized by Ohkawara Kakohki Co., Ltd., Kanagawa, Japan. The spray-drying was carried out by an atomizer-system with conditions of inlet temperature of 180° C., outlet temperature of 90° C., and feeding speed of 2 L/hour. The resulting powder was aged at a temperature of 25° C. in a relative humidity of 60% for seven days, and successively dried in vacuo at 25° C. for 18 hours to make into a particulate composition containing crystalline trehalose dihydrate.

The emulsifying ability, degree of crystallinity for crystalline trehalose dihydrate, and specific surface area of the product were determined to be 0.48, 69.6%, and 0.50 $m^2/g$, respectively. The product was subjected to a particle size distribution measurement and was revealed that it contained particles with a particle size of at least 53 μm but smaller than 300 μm in an amount of 68% by weight based on the particulate composition as a whole, and particles with a particle size of smaller than 53 μm in an amount of 15% by weight based on the particulate composition as a whole. Since the product has an advantageous emulsifying ability, it can be advantageously used for the production of, particularly, foods and cosmetics, rich in fats and oils. The product can be arbitrary used as a material for foods and cosmetics as in the cases of conventional particulate composition containing crystalline trehalose dihydrate.

Example 5

<Powdery Potage Soup>

To a mixture of 35 parts by weight of pre-gelatinized corn starch powder, 12 parts by weight of pre-gelatinized waxy-corn starch, 4 parts by weight of pre-gelatinized potato starch powder, 10 parts by weight of the particulate composition containing crystalline trehalose dihydrate, obtained in Example 1, 7 parts by weight of skimmed milk, 7 parts by weight of sodium chloride, and 0.5 part by weight of onion powder; 10 parts by weight of melted vegetable hardened oil was further added and mixed, and then the resulting mixture was granulated by a fluid bed granulator, dried in 70° C. hot air to make into a powdery potage soup.

Since the oily ingredients in the product dispersed homogeneously when the product was dissolved in hot water, the product can be used as a powdery corn potage soup with a smooth taste and a preferable flavor.

Example 6

<Bath Additive>

Fifteen parts by weight of the particulate composition containing crystalline trehalose dihydrate, obtained in Example 1-1, and 5 parts by weight of fumaric acid were put into a Nauta mixer and mixed by stirring at 100 rpm and the jacket temperature of 55° C. Successively, the resulting mixture was gradually admixed with 3 parts by weight of isopropyl palmitate and one part by weight of octyldodecyl myristate, and further admixed with adequate amount of flavors in the mixer. Then, the resulting mixture was granulated by an extrusion granulator to make into a bath additive.

Since the oily ingredients in the product dispersed homogeneously when the product was dissolved in hot water, the product can be used as a bath additive with a good availability to give a smooth fluidity of hot water.

Reference Example 1

<Particulate Composition Containing Crystalline Trehalose Dihydrate>

Except for changing the aging period to 5 days, a particulate composition containing crystalline trehalose dihydrate was prepared by the same method in Example 4. The emulsifying ability and crystallinity for crystalline trehalose dihydrate of the product were determined to be 0.28 and 68.8%, respectively, and it was revealed that the emulsifying ability of the product was not advantageous.

As is evident from Example 4 and Reference Example 1, in the case of aging the pulverized saccharide for 5 days, a particulate composition having an advantageous emulsifying ability was never obtained by admixing seed crystals with the trehalose-containing solution and successively spray-drying the resulting massecuites. On the other hand, in the case of aging the pulverized saccharide for 7 days or longer, a particulate composition having an advantageous emulsifying ability was obtained. These results indicate that, for producing a particulate composition having an advantageous emulsifying ability, a process for aging the powder, obtained by spray-drying a trehalose-containing solution, under a relative humidity of 60% or higher for 7 days or longer is important with or without adding seed crystals.

INDUSTRIAL APPLICABILITY

As described above, since the particulate composition containing crystalline trehalose dihydrate of the present invention has an advantageous emulsifying ability, it can be expected that the particulate composition will be used effectively in various fields such as foods and beverages, cosmetics, etc. Thus, the present invention is a significantly important invention that greatly contributes to this art.

The invention claimed is:

1. A particulate composition comprising crystalline α,α-trehalose dihydrate, which consists of particles containing α,α-trehalose and maltose and/or maltotriose, and has the following characteristics (1) to (3):
    (1) comprising α,α-trehalose in an amount of 70% by weight or higher but 90% by weight or lower, on a dry solid basis;
    (2) comprising maltose and/or maltotriose in a total amount of 3% by weight or higher, on a dry solid basis; and (3) having a degree of crystallinity for crystalline α,α-trehalose dihydrate of 25% or higher but less than 90%, when calculated based on its powder X-ray diffraction profile.

2. The particulate composition of claim 1, which has the following characteristic (4):
   (4) having a specific surface area of 0.25 m$^2$/g or higher when determined by the gas adsorption isotherms using nitrogen.

3. The particulate composition of claim 1, which has the following characteristic (5):
   (5) containing particles with a particle size of at least 53 μm but smaller than 300 μm in an amount of 50% by weight or higher based on the particulate composition as a whole, and particles with a particle size of smaller than 53 μm in an amount of 10% by weight or higher based on the particulate composition as a whole.

4. The particulate composition of claim 1, which has the following characteristic (6):
   (6) the turbidity at 720 nm of the emulsion is 0.35 or higher, when an emulsion is prepared by the steps of mixing five parts by weight of said particulate composition and one part by weight of corn oil, admixing with 500 parts by weight of purified water, and stirring the mixture.

5. An emulsifier, comprising the particulate composition of claim 1.

6. A process for producing the particulate composition of claim 1, comprising the steps of:
   preparing a saccharide solution containing α,α-trehalose in an amount of 70% by weight or higher but 90% by weight or lower, on a dry solid basis, and maltose and/or maltotriose in a total amount of 3% by weight or higher, on a dry solid basis;
   spray-drying said saccharide solution to form particulate composition;
   crystallizing α,α-trehalose to form crystalline α,α-trehalose dihydrate by aging the resulting particulate composition under a relative humidity of 60% or higher for 7 days or longer; and
   drying the resulting particulate composition comprising crystalline α,α-trehalose dihydrate.

7. The process of claim 6, wherein said step of preparing a saccharide solution containing α,α-trehalose in an amount of 70% by weight or higher but 90% by weight or lower, on a dry solid basis, and maltose and/or maltotriose in a total amount of 3% by weight or higher, on a dry solid basis, is conducted by allowing glycosyltrehalose-forming enzyme and trehalose-releasing enzyme to act on liquefied starch together with starch-debranching enzyme and cyclomaltodextrin glucanotransferase.

8. The process of claim 6, wherein said step of spray-drying is conducted by using a rotary atomizer system.

* * * * *